United States Patent
Liu et al.

(10) Patent No.: US 12,226,530 B2
(45) Date of Patent: Feb. 18, 2025

(54) LENALIDOMIDE GASTRO-RETENTIVE SUSTAINED-RELEASE TABLET AND PREPARATION METHOD THEREOF

(71) Applicant: DiQi Pharmaceuticals Co., Ltd., Guangdong (CN)

(72) Inventors: Feng Liu, Guangdong (CN); Huafeng Luo, Guangdong (CN); Jingyu He, Guangdong (CN); Xiaofeng Tan, Guangdong (CN); Shuting Lai, Guangdong (CN)

(73) Assignee: DIQI PHARMACEUTICALS CO., LTD., Guangdong (CN)

( * ) Notice: Subject to any disclaimer, the term of this patent is extended or adjusted under 35 U.S.C. 154(b) by 356 days.

(21) Appl. No.: 17/041,635

(22) PCT Filed: Sep. 29, 2018

(86) PCT No.: PCT/CN2018/108771
§ 371 (c)(1),
(2) Date: Sep. 25, 2020

(87) PCT Pub. No.: WO2019/218576
PCT Pub. Date: Nov. 21, 2019

(65) Prior Publication Data
US 2021/0128476 A1    May 6, 2021

(30) Foreign Application Priority Data
May 17, 2018 (CN) .......................... 201810471714.9

(51) Int. Cl.
*A61K 9/20* (2006.01)
*A61K 9/00* (2006.01)
*A61K 31/454* (2006.01)

(52) U.S. Cl.
CPC .......... *A61K 9/2054* (2013.01); *A61K 9/0065* (2013.01); *A61K 9/2095* (2013.01); *A61K 31/454* (2013.01)

(58) Field of Classification Search
None
See application file for complete search history.

(56) References Cited

U.S. PATENT DOCUMENTS 9,068,021 B2 * 6/2015 Maruyama ............... C08B 11/08
2017/0107193 A1 * 4/2017 Rampalli ............. C07D 401/04

FOREIGN PATENT DOCUMENTS

| CN | 103610658 | 3/2014 |
| CN | 108514560 | 9/2018 |
| WO | WO2010054833 | * 5/2010 |

OTHER PUBLICATIONS

Sahoo et al. (Journal of Chemical and Pharmaceutical Sciences, 8(4), 875-881, 2015).*
Arora et al. (AAPS PharmSciTech 2005; 6 (3) Article 47) Floating Drug Delivery Systems: A Review.*
Baumgartner et al. (International Journal of Pharmaceutics 195 (2000) 125-135) Optimisation of floating matrix tablets and evaluation of their gastric residence time.*
Product Specification of Avicel® PH-101 (from Dupont issued on Jun. 1, 2017).*
Jindal et al. (Marmara Pharmaceutical Journal 20: 100-110, 2016) Gastroretentive floating tablets: An investigation of excipients effect on tablet properties.*
International Search Report filed in PCT/CN2018/108771 mailed Feb. 18, 2019.

* cited by examiner

*Primary Examiner* — Tigabu Kassa
(74) *Attorney, Agent, or Firm* — RANKIN, HILL & CLARK LLP

(57) ABSTRACT

The invention discloses a lenalidomide gastro-retentive sustained-release tablet and a preparation method thereof. The sustained-release tablet comprises 3 wt % to 14 wt % of lenalidomide, 14 wt % to 68 wt % of release enhancer with low bulk density, 23 wt % to 70 wt % of sustained-release material with low bulk density, and the balance of other pharmaceutically acceptable excipients, wherein the bulk density of the release enhancer ranges from 0.24 $g/cm^3$ to 0.52 $g/cm^3$; and the bulk density of the sustained-release material ranges from 0.29 $g/cm^3$ to 0.51 $g/cm^3$. The sustained-release tablet of the invention is in a floating state in a gastric environment, is not directly discharged from a stomach due to gastric emptying, has an effect of gastric retention, and is not easily discharged with substances contained in the stomach, and has a high drug bioavailability and small side effects.

10 Claims, No Drawings

LENALIDOMIDE GASTRO-RETENTIVE SUSTAINED-RELEASE TABLET AND PREPARATION METHOD THEREOF

TECHNICAL FIELD

The present invention belongs to the field of medical technologies, and more particularly, relates to a lenalidomide gastro-retentive sustained-release tablet and a preparation method thereof.

BACKGROUND

As an anti-tumor immunomodulator developed by Celgene and marketed in a capsule form, lenalidomide has been widely used in multiple myeloma (MM) clinically.

Commercially available lenalidomide capsules are absorbed quickly in a gastrointestinal tract after oral administration, which have a peak time of 0.5 hour to 1.5 hours and a half-life period of about 3 hours. When a dosage ranges from 5 mg to 50 mg, both a maximum plasma concentration (Cmax) and an area under curve (AUC) may be increased proportionally with the increase of the dosage. However, the blood concentration fluctuates greatly, and toxic and side effects are obvious, so that a number of neutrophils and a number of blood platelets are decreased obviously. Therefore, it is necessary to prepare a sustained-release preparation with small blood concentration fluctuations, so as to reduce a peak-valley difference of the blood concentration, realize a stable blood concentration and reduce the toxic and side effects.

An oral sustained-release preparation refers to a preparation capable of releasing a drug continuously for a long time after administration. The drug in the sustained-release preparation is slowly released at an appropriate speed, which reduces peak-valley phenomena of the blood concentration in the administration of an ordinary dosage form, keeps the blood concentration in a relatively stable and lasting effective range, and improves a safety of the drug. Administration times of sustained-release preparation prepared from the drug having a short biological half-life period or needing frequent administration can be reduced, such that a medication compliance is improved.

Patent CN103610658A provides a lenalidomide sustained-release preparation and a preparation method thereof. A drug in a lenalidomide sustained-release tablet according to this invention may be slowly and uniformly released by using a sustained-release framework material, so that a release speed is reduced, a time peak is delayed, an action time of the lenalidomide is prolonged and a uniform and constant blood concentration is provided. However, a retention time of a conventional sustained-release preparation in an upper digestive tract (stomach and duodenum) of a human body is short due to influences of gastric emptying and intestinal tract transportation, and some drugs have been transported to a lower digestive tract even before being released from the tablet or absorbed completely, so that a best absorption site is missed, resulting in the decrease of an area under curve (AUC) and a bioavailability, thus affecting a therapeutic effect of the drug.

A gastro-retentive sustained-release preparation belongs to the category of the sustained-release preparation, has a characteristic of being localized and released in a stomach, and is able to prolong a release time of the drug in a gastrointestinal tract (mainly the stomach), thus improving an absorption degree of the drug in the gastrointestinal tract. The drug is released continuously in the stomach, thus reducing an influence of a pH value of a body fluid on a drug release rate and improving a bioavailability or a therapeutic effect of some drugs. A stability of some active substances (such as lenalidomide and captopril) is decreased with the increase of a pH in an intestinal environment. When the active substances are prepared into a gastro-retentive sustained-release preparation, active ingredients may be released and absorbed in a low-pH environment, thus improving the bioavailability. It is very important to prolong a retention time of a drug with a local activity (such as L-dopa or riboflavin having an absorption window in an upper intestinal tract) in the stomach.

A solubility of the lenalidomide in a hydrochloric acid buffer with a pH of 1.2 is about 18 mg/ml. When a pH of a solution medium is greater than 4.6, the solubility of the lenalidomide is lower than 0.6 mg/ml. The stability of the lenalidomide is related to a pH of a solvent, and the degradation of the lenalidomide is intensified when the pH is increased. A concentration of the lenalidomide is unchanged for 6 hours in a solvent with a pH of 1.2, the concentration is decreased by 6% when being stayed in a solvent with a pH of 4.5 for 6 hours, and the concentration is decreased by 16% when being in a solvent with a pH of 6.8 for 6 hours. Under a normal physiological condition, a pH value in stomach is about 1 to 4, and a pH value in the intestinal tract is about 5 to 8. The stability and the solubility of the lenalidomide in the stomach are better than those in the intestinal tract. Therefore, compared with an ordinary sustained-release tablet, the lenalidomide sustained-release tablet with a gastro-retentive function is able to better ensure the stability of the active ingredients after release while keeping the sustained-release effect, such that the bioavailability is improved and possible toxic and side effects brought by degradation products are reduced.

At present, major retention principles of the gastro-retentive preparation are biological adhesion, size rejection and floating. A bio-adhesive gastro-retentive sustained-release preparation may adhere to substances contained in the stomach due to a non-selectivity of adhesion thereof and be discharged from the stomach by gastric peristalsis. A size-rejection gastro-retentive sustained-release preparation is not conducive for a patient to swallow due to a big size thereof, and has a risk of blocking a pylorus of the stomach at the same time, thus affecting normal operation of gastric peristalsis. A floating gastro-retentive sustained-release preparation is composed of a light waxy material (floating assistant) or carbonate (foaming agent) capable of generating gases. The commonly used floating assistant comprises octadecanol, stearic acid, glyceryl monostearate, glyceryl behenate, carnauba wax, white wax, hydrogenated vegetable oil, and the like. These substances have poor stability and low melting point, which are not conducive to the stability of the preparation and production. The commonly used foaming agent is alkaline carbonate or bicarbonate, which is not suitable for drugs unstable to alkali.

SUMMARY

Objective: in order to solve the technical problems in the prior art, the present invention provides a lenalidomide gastro-retentive sustained-release tablet and a preparation method thereof, wherein the sustained-release tablet provided can float quickly in a gastric environment, which presents a floating state, has a long retention time in a stomach, which is difficult to discharge with substances contained in the stomach, and meanwhile, has a high drug bioavailability and small side effects.

Technical solution: in order to achieve the above technical objective, a lenalidomide gastro-retentive sustained-release tablet is provided, wherein the sustained-release tablet comprises 3 wt % to 14 wt % of lenalidomide, 14 wt % to 68 wt % of release enhancer with low bulk density, 23 wt % to 70 wt % of sustained-release material with low bulk density, and the balance of other pharmaceutically acceptable excipients. Preferably, a dosage of the release enhancer accounts for 40% to 68% of a prescription weight, and the bulk density of the release enhancer ranges from 0.24 g/cm³ to 0.52 g/cm³; and preferably, a dosage of the sustained-release material accounts for 30% to 50% of the prescription weight, and the bulk density of the sustained release material ranges from 0.29 g/cm³ to 0.51 g/cm³.

A crystal form of the lenalidomide comprises a crystal form A, a crystal form B, a crystal form E, a crystal form F, a crystal form H, a crystal form I, a crystal form II, a crystal form IV, a crystal form X and a crystal form α, preferably the crystal form B, the crystal form IV, the crystal form α, the crystal form I and the crystal form II, and more preferably the crystal form B.

Physical properties of different crystal forms of the lenalidomide are as follows.

Crystal form A: in an X-ray diffraction pattern thereof, 2θ expressed by degrees has characteristic absorption peaks at about 8, 14.5, 16, 17.5, 20.5, 24 and 26, and a melting point of about 270□.

Crystal form B: a semi-hydrate, wherein in an X-ray diffraction pattern thereof, 2θ expressed by degrees has characteristic absorption peaks at about 16, 18, 22 and 27, and a melting point of about 267□.

Crystal form H: a melting point thereof is about 269□, a DSC thermogram shows that heat absorption occurs at about 50□ to about 125□ and occurs at about 269□, wherein in an X-ray diffraction pattern thereof, 2θ expressed by degrees has characteristic absorption peaks at about 12.5, 15.2, 26 and 31.

Crystal form E: in an X-ray diffraction pattern thereof, 2θ expressed by degrees has characteristic absorption peaks at about 20, 24.5 and 29.

Crystal form F: in an X-ray diffraction pattern thereof, 2θ expressed by degrees has characteristic absorption peaks at about 19, 19.5 and 25.

Crystal form X: in an X-ray diffraction pattern thereof, 2θ expressed by degrees has diffraction peaks at about 12.0, 14.3, 14.8, 16.2, 17.6, 21.5, 22.6, 23.8, 24.0, 26.0, 28.3, 29.8, 31.9, 32.6 and 33.5.

Crystal form I: in an X-ray diffraction pattern thereof, 2θ expressed by degrees has diffraction peaks at about 7.9, 8.6, 14.2, 14.5, 15.8, 17.0, 18.0, 18.4, 18.8, 19.6, 21.6, 22.0, 22.9, 23.3, 24.0, 24.4, 25.4, 26.8, 29.1, 29.6, 30.2, 31.0 and 32.0, and a melting point ranging from 267□ to 269□.

Crystal form α: in an X-ray diffraction pattern thereof, 2θ expressed by degrees has diffraction peaks at about 10.1, 12.4, 17.3, 18.1, 18.4, 19.7, 21.5, 22.9, 24.5, 25.6, 26.6, 27.9 and 32.4.

Crystal form □: in an X-ray diffraction pattern thereof, 2θ expressed by degrees has diffraction peaks at about 12.0, 12.5, 13.2, 13.6, 15.2, 15.7, 17.1, 18.0, 18.9, 19.5, 19.9, 25.6, 28.6, 29.1, 30.2, 30.6, 31.0, 31.9, 34.1 and 34.5, and a melting point ranging from 267□ to 269□.

Crystal form □: in an X-ray diffraction pattern thereof, 2θ expressed by degrees has diffraction peaks at about 7.7±0.2, 11.9±0.2, 25.8±0.2, 15.6±0.2, 16.4±0.2, 17.6±0.2, 20.4±0.2, 21.2±0.2, 24.0±0.2, 24.7±0.2, 27.4±0.2 and 29.0±0.2, and DSC scanning thereof shows that a first endothermic peak is in a range from 115□ to 142□, and a second endothermic peak is in a range from 261□ to 271□.

The release enhancer is insoluble in water, and a volume of the release enhancer is expanded after the release enhancer is contacted with water, which makes a volume of the tablet be further expanded, thus increasing a contact area between the tablet and gastric juice, and promoting the drug to release. Meanwhile, a density of the tablet is further reduced due to the volume expansion of the tablet, which enables the tablet to keep in a floating state in the gastric juice, so that a release time of the tablet in the stomach is prolonged.

Specifically, the release enhancer is selected from one or more of crospovidone, microcrystalline cellulose, low-substituted hydroxypropyl cellulose and croscarmellose sodium. Preferably, the release enhancer is one or a combination of the crospovidone and the microcrystalline cellulose. When the release enhancer preparation is a combination of the crospovidone and the microcrystalline cellulose, a ratio of the crospovidone to the microcrystalline cellulose is 1:9 to 4:1. The sustained-release material is any one or a combination of hydroxypropyl methylcellulose, polyethylene oxide, hydroxypropyl cellulose, hydroxyethyl cellulose and sodium carboxymethylcellulose. Preferably, the sustained-release material is the hydroxypropyl methylcellulose.

In a preferred embodiment, the sustained-release material is the hydroxypropyl methylcellulose, and a weight-average molecular weight thereof is greater than or equal to 200,000. Preferably, a viscosity of 2% aqueous solution of the sodium carboxymethylcellulose, the hydroxypropyl cellulose and the hydroxyethyl cellulose is greater than 3000 mPa·s.

A hardness of the lenalidomide gastro-retentive sustained-release tablet ranges from 3 kg/cm² to 10 kg/cm². Preferably, the lenalidomide gastro-retentive sustained-release tablet is prepared into a sustained-release tablet with a hardness ranging from 5 kg/cm² to 6 kg/cm².

Preferably, a density of the lenalidomide gastro-retentive sustained-release tablet ranges from 0.755 g/cm³ to 0.991 g/cm³.

Specifically, the other pharmaceutically acceptable excipients comprise a lubricant and a glidant.

The glidant is selected from one or a combination of silicon dioxide, talcum, etc., and is preferably the silicon dioxide. A dosage of the glidant accounts for 0.6% to 2.5% of a prescription weight.

The lubricant is selected from one or a combination of magnesium stearate, sodium stearyl fumarate, talcum, etc., and is preferably the magnesium stearate. A dosage of the lubricant accounts for 0.6% to 4.0% of the prescription weight.

The present invention further proposes a method for preparing the above lenalidomide gastro-retentive sustained-release tablet, which comprises the following steps of:

(1) sieving raw materials and the excipients respectively, by using a 60-mesh sieve preferably;

(2) mixing a prescription amount of active pharmaceutical ingredient with all excipients excluding the lubricant to form a uniform blend;

(3) adding a prescription amount of lubricant into the blend for proper mixing to obtain a total blend; and (4) pressing the total blend into a tablet.

Preferably, a hardness of the pressed tablet ranges from 3 kg/cm² to 10 kg/cm² and a density of the pressed tablet ranges from 0.755 g/cm³ to 0.991 g/cm³.

Further, the prepared tablet may be further coated by a conventional method.

A coating agent used in the coating is preferably gastric-soluble Opadry. A proper amount of lenalidomide may be added while preparing a coating solution, so that a coating layer of the coated tablet contains the lenalidomide to form a coating quick-release layer, thus realizing effects of quick-release and sustained-release of the lenalidomide.

Each lenalidomide gastro-retentive sustained-release tablet of the present invention comprises 5 mg to 30 mg of lenalidomide and is administrated in every 24 hours. The lenalidomide gastro-retentive sustained-release tablet of the present invention is used for treating transfusion-dependent anemia which is already treated by one therapy and is caused by myelodysplastic syndrome (MSD) with low risk or moderate-1 risk due to 5q chromosome deletion and/or other cytogenetic abnormalities; may be combined with dexamethasone to treat multiple myeloma (MM); and may also be used for treating recurrent and progressive mantle cell lymphoma (MCL) after two treatments comprising once bortezomib therapy.

Compared with the prior art, the lenalidomide gastro-retentive sustained-release tablet has the following characteristics that: the lenalidomide gastro-retentive sustained-release tablet can float quickly in the stomach environment in the floating state; is moderate in size, has no dysphagia, and has a high patient compliance; has a long gastro-retentive time and is not easy to be discharged with the substances contained in the stomach; does not contain floating assistants with low melting point (such as a waxy material), has a high storage stability and a long shelf life; does not contain alkaline foaming agents, and is suitable for drugs unstable to alkali; and has a high drug bioavailability and small side effects.

DETAILED DESCRIPTION

The present invention is further described in detail hereinafter with reference to the embodiments.

A method for determining bulk densities of a sustained-release material and a release enhancer in the present invention is as follows: filling 100 ml of sustained-release material or release enhancer into a 100 ml measuring cylinder, then weighing the 100 ml of sustained-release material or release enhancer, and dividing a weight of the 100 ml of sustained-release material or release enhancer by a volume thereof to obtain the bulk density.

A density of the tablet in the present invention is determined by a JT-1200EN multi-functional solid apparent density tester (MatsuHaku, Taiwan).

An in-vitro floating performance and an in-vitro release effect of the lenalidomide gastro-retentive sustained-release tablet of the present invention are determined with reference to the Second Method in the Four General Principles of the Chinese Pharmacopoeia (Edition 2015).

A specific inspection method for the in-vitro floating performance is to observe how long can the sustained-release tablet after being put into a dissolution cup containing a dissolution medium float up, and how long can the sustained-release tablet=to float in liquid.

Specific inspection conditions for the in-vitro release rate are as follows: 500 ml of hydrochloric acid solution with a pH of 1.2 is used as the dissolution medium, and a rotating speed of a dissolution device is 100 r/min, and operations shall be carried out according to law. 5 ml of solution is respectively taken at specified time points, and filtered, and 5 ml of the same solvent with the same temperature is added into the operating container immediately. A content of a filtrate is determined, and the release rate of the tablet is calculated.

Embodiment 1

| Lenalidomide | 5 g |
| Sodium carboxymethylcellulose | 82 g |
| Microcrystalline cellulose | 144 g |
| Hydroxypropyl methylcellulose | 85 g |
| Crospovidone | 36 g |
| Silicon dioxide | 7 g |
| Magnesium stearate | 7 g |
| Finished products | 1000 tablets |

Information of Release Enhancer and Sustained-Release Material:

| Trade name | Category | Model | Bulk density (g/cm³) |
| --- | --- | --- | --- |
| Sodium carboxymethylcellulose | Sustained-release material | SJJ-H | 0.51 |
| Microcrystalline cellulose | Release enhancer | 101 | 0.39 |
| Hydroxypropyl methylcellulose | Sustained-release material | K200M | 0.29 |
| Crospovidone | Release enhancer | XL | 0.32 |

Lenalidomide in crystal form B was used, and a weight-average molecular weight of the hydroxypropyl methylcellulose K200M was about 1,200,000. A preparation method of tablets was as follows: weighing the above raw materials and excipients excluding the magnesium stearate, sieving the same with a 60-mesh sieve respectively and mixing uniformly, then adding the magnesium stearate and mixing properly, and pressing the mixture into tablets with a hardness of 9 kg/cm² to 10 kg/cm² and a density of 0.991 g/cm³.

Floating performance of gastro-floating sustained-release tablet in Embodiment 1: the tablets floated up quickly after being put into a dissolution cup, and floated continuously in a dissolution medium for at least 24 hours.

Determination Results of Release Rate of the Lenalidomide Gastro-Retentive Sustained-Release Tablet Prepared According to Embodiment 1:

| Time (h) | 2 | 4 | 8 | 12 | 16 | 20 | 24 |
| --- | --- | --- | --- | --- | --- | --- | --- |
| Drug release percentage (%) | 10.3 | 20.9 | 42.6 | 63.5 | 79.8 | 91.9 | 94.2 |

The determination results show that the lenalidomide gastro-retentive sustained-release tablet has a significant sustained-release characteristic, and it will take about 16 hours to release 80% of the drugs in the tablet.

Embodiment 2

| Lenalidomide | 25 g |
| Crospovidone | 26 g |
| Hydroxypropyl methylcellulose | 128 g |
| Silicon dioxide | 2 g |
| Sodium stearyl fumarate | 2 g |
| Finished products | 1000 tablets |

Information of Release Enhancer and Sustained-Release Material:

| Trade name | Category | Model | Bulk density (g/cm³) |
|---|---|---|---|
| Hydroxypropyl methylcellulose | Sustained-release material | K250 | 0.29 |
| Crospovidone | Release enhancer | SL-10 | 0.24 |

Lenalidomide in crystal form A was used, and a weight-average molecular weight of the hydroxypropyl methylcellulose K250 was about 200,000. A preparation method of tablets was as follows: weighing the above raw materials and excipients excluding the sodium stearyl fumarate, sieving the same with a 60-mesh sieve respectively and mixing uniformly, then adding the sodium stearyl fumarate and mixing properly, and pressing the mixture into tablets with a hardness of 3 kg/cm² to 4 kg/cm² and a density of 0.755 g/cm³.

Floating performances of gastro-floating sustained-release tablets in Embodiment 2: the tablet floated up quickly after being put into a dissolution cup, and floated continuously in a dissolution medium for at least 24 hours.

Determination Results of Release Rate of the Lenalidomide Gastro-Retentive Sustained-Release Tablet Prepared According to Embodiment 2:

| Time (h) | 2 | 4 | 8 | 12 | 16 | 20 | 24 |
|---|---|---|---|---|---|---|---|
| Drug release percentage (%) | 16.3 | 28.9 | 52.6 | 74.5 | 90.1 | 95.8 | 96.6 |

The determination results show that the lenalidomide gastro-retentive sustained-release tablet has a significant sustained-release characteristic, and it will take about 14 hours to release 80% of the drugs in the tablet.

Embodiment 3

| Lenalidomide | 15 g |
|---|---|
| Sodium carboxymethylcellulose | 25 g |
| Croscarmellose sodium | 70 g |
| Hydroxypropyl methylcellulose | 150 g |
| Silicon dioxide | 7 g |
| talcum | 11 g |
| Finished products | 1000 tablets |

Information of Release Enhancer and Sustained-Release Material:

| Trade name | Category | Model | Bulk density (g/cm³) |
|---|---|---|---|
| Sodium carboxymethylcellulose | Sustained-release material | 7HXF | 0.48 |
| Croscarmellose sodium | Release enhancer | SD 711 | 0.52 |
| Hydroxypropyl methylcellulose | Sustained-release material | K750 | 0.29 |

Lenalidomide in crystal form II was used, and a weight-average molecular weight of the hydroxypropyl methylcellulose K750 was about 250,000. A preparation method of tablets was as follows: weighing the above raw materials and excipients excluding the talcum, sieving the same with a 60-mesh sieve respectively and mixing uniformly, then adding the talcum and mixing properly, and pressing the mixture into tablets with a hardness of 5 kg/cm² to 6 kg/cm² and a density of 0.949 g/cm³.

Floating performance of gastro-floating sustained-release tablet in Embodiment 3: the tablet floated up quickly after being put into a dissolution cup, and floated continuously in a dissolution medium for at least 24 hours.

Determination Results of Release Rate of the Lenalidomide Gastro-Retentive Sustained-Release Tablets Prepared According to Embodiment 3:

| Time (h) | 2 | 4 | 8 | 12 | 16 | 20 | 24 |
|---|---|---|---|---|---|---|---|
| Drug release percentage (%) | 14 | 26.3 | 47.6 | 67.6 | 84.9 | 90.1 | 93.7 |

The determination results show that the lenalidomide gastro-retentive sustained-release tablet has a significant sustained-release characteristic, and it will take about 16 hours to release 80% of the drugs in the tablet.

Embodiment 4

| Lenalidomide | 20 g |
|---|---|
| Low-substituted hydroxypropyl cellulose | 101 g |
| Hydroxypropyl cellulose | 65 g |
| Silicon dioxide | 2 g |
| Magnesium stearate | 2 g |
| Finished products | 1000 tablets |

Information of Release Enhancer and Sustained-Release Material:

| Trade name | Category | Model | Bulk density (g/cm³) |
|---|---|---|---|
| Hydroxypropyl cellulose | Sustained-release material | MF | 0.41 |
| Low-substituted hydroxypropyl cellulose | Release enhancer | 102 | 0.36 |

Lenalidomide in crystal form E was used. A preparation method of tablets was as follows: weighing the above raw materials and excipients excluding the magnesium stearate, sieving the same with a 60-mesh sieve respectively and mixing uniformly, then adding the magnesium stearate and mixing properly, and pressing the mixture into tablets with a hardness of 3 kg/cm² to 4 kg/cm² and a density of 0.836 g/cm³. Floating performance of gastro-floating sustained-release tablet in Embodiment 4: the tablet floated up quickly after being put into a dissolution cup, and floated continuously in a dissolution medium for at least 24 hours.

Determination Results of Release Rate of the Lenalidomide Gastro-Retentive Sustained-Release Tablets Prepared According to Embodiment 4:

| Time (h) | 2 | 4 | 8 | 12 | 16 | 20 | 24 |
|---|---|---|---|---|---|---|---|
| Drug release percentage (%) | 15.7 | 27.6 | 49.3 | 69 | 83.2 | 94.5 | 94.9 |

The determination results show that the lenalidomide gastro-retentive sustained-release tablet has a significant sustained-release characteristic, and it will take about 16 hours to release 80% of the drugs in the tablet.

Embodiment 5

| Lenalidomide | 25 g |
| Microcrystalline cellulose | 220 g |
| Hydroxypropyl methylcellulose | 75 g |
| Silicon dioxide | 2 g |
| Magnesium stearate | 2 g |
| Finished products | 1000 tablets |

Information of Release Enhancer and Sustained-Release Material:

| Trade name | Category | Model | Bulk density (g/cm$^3$) |
| --- | --- | --- | --- |
| Hydroxypropyl methylcellulose | Sustained-release material | K100M | 0.29 |
| Microcrystalline cellulose | Release enhancer | 102 | 0.36 |

Lenalidomide in crystal form □ was used, and a weight-average molecular weight of the hydroxypropyl methylcellulose K100M was about 1,000,000. A preparation method of tablets was as follows: weighing the above raw materials and excipients excluding the magnesium stearate, sieving the same with a 60-mesh sieve respectively and mixing uniformly, then adding the magnesium stearate and mixing properly, and pressing the mixture into tablets with a hardness of 7 kg/cm$^2$ to 8 kg/cm$^2$ and a density of 0.966 g/cm$^3$.

Floating performance of gastro-floating sustained-release tablet in Embodiment 5: the tablet floated up quickly after being put into a dissolution cup, and floated continuously in a dissolution medium for at least 24 hours.

Determination Results of Release Rate of the Lenalidomide Gastro-Retentive Sustained-Release Tablets Prepared According to Embodiment 5:

| Time (h) | 2 | 4 | 8 | 12 | 16 | 20 | 24 |
| --- | --- | --- | --- | --- | --- | --- | --- |
| Drug release percentage (%) | 17 | 28.9 | 49.4 | 67.1 | 80.8 | 91.9 | 95.6 |

The determination results show that the lenalidomide gastro-retentive sustained-release tablet has a significant sustained-release characteristic, and it will take about 16 hours to release 80% of the drugs in the tablet.

Embodiment 6

| Lenalidomide | 10 g |
| Hydroxyethyl cellulose | 50 g |
| Microcrystalline cellulose | 200 g |
| Hydroxypropyl methylcellulose | 60 g |
| Magnesium stearate | 2 g |
| Finished products | 1000 tablets |

Information of Release Enhancer and Sustained-Release Material:

| Trade name | Category | Model | Bulk density (g/cm$^3$) |
| --- | --- | --- | --- |
| Hydroxypropyl methylcellulose | Sustained-release material | K100M | 0.29 |
| Microcrystalline cellulose | Release enhancer | 102 | 0.36 |
| Hydroxyethyl cellulose | Sustained-release material | HHW | 0.51 |

Lenalidomide in crystal form □ was used. A preparation method of tablets was as follows: weighing the above raw materials and excipients excluding the magnesium stearate, sieving the same with a 60-mesh sieve respectively and mixing uniformly, then adding the magnesium stearate and mixing properly, and pressing the mixture into tablets with a hardness of 6 kg/cm$^2$ to 7 kg/cm$^2$ and a density of 0.977 g/cm$^3$. Floating performance of gastro-floating sustained-release tablet in Embodiment 6: the tablet floated up quickly after being put into a dissolution cup, and floated continuously in a dissolution medium for at least 24 hours.

Determination Results of Release Rate of the Lenalidomide Gastro-Retentive Sustained-Release Tablets Prepared According to Embodiment 6:

| Time (h) | 2 | 4 | 8 | 12 | 16 | 20 | 24 |
| --- | --- | --- | --- | --- | --- | --- | --- |
| Drug release percentage (%) | 18.3 | 30.1 | 52.3 | 67.4 | 80.9 | 92.7 | 95.1 |

The determination results show that the lenalidomide gastro-retentive sustained-release tablet has a significant sustained-release characteristic, and it will take about 18 hours to release 80% of the drugs in the tablet.

Embodiment 7

| Lenalidomide | 20 g |
| Microcrystalline cellulose | 150 g |
| Polyethylene oxide | 50 g |
| Hydroxypropyl methylcellulose | 70 g |
| Silicon dioxide | 4 g |
| Magnesium stearate | 4 g |
| Finished products | 1000 tablets |

Information of Release Enhancer and Sustained-Release Material:

| Trade name | Category | Model | Bulk density (g/cm$^3$) |
| --- | --- | --- | --- |
| Hydroxypropyl methylcellulose | Sustained-release material | K4M | 0.32 |
| Microcrystalline cellulose | Release enhancer | 102 | 0.36 |
| Polyethylene oxide | Sustained-release material | 470 | 0.45 |

Lenalidomide in crystal form □ was used, and a weight-average molecular weight of the hydroxypropyl methylcellulose K4M was about 400,000. A preparation method of tablets was as follows: weighing the above raw materials and excipients excluding the magnesium stearate, sieving the same with a 60-mesh sieve respectively and mixing uniformly, then adding the magnesium stearate and mixing properly, and pressing the mixture into tablets with a hardness of 5 kg/cm² to 6 kg/cm² and a density of 0.930 g/cm³.

Floating performance of gastro-floating sustained-release tablet in Embodiment 7: the tablet floated up quickly after being put into a dissolution cup, and floated continuously in a dissolution medium for at least 24 hours.

Determination Results of Release Rate of the Lenalidomide Gastro-Retentive Sustained-Release Tablets Prepared According to Embodiment 7:

| Time (h) | 2 | 4 | 8 | 12 | 16 | 20 | 24 |
|---|---|---|---|---|---|---|---|
| Drug release percentage (%) | 19.6 | 32.9 | 58.7 | 75.4 | 89.4 | 94.7 | 95.8 |

The determination results show that the lenalidomide gastro-retentive sustained-release tablet has a significant sustained-release characteristic, and it will take about 14 hours to release 80% of the drugs in the tablet.

Embodiment 8

| Lenalidomide | 25 g |
|---|---|
| Crospovidone | 74 g |
| Hydroxypropyl methylcellulose | 98 g |
| Silicon dioxide | 2 g |
| Sodium stearyl fumarate | 2 g |
| Finished products | 1000 tablets |

Information of Release Enhancer and Sustained-Release Material:

| Trade name | Category | Model | Bulk density (g/cm³) |
|---|---|---|---|
| Hydroxypropyl methylcellulose | Sustained-release material | K1500 | 0.29 |
| Crospovidone | Release enhancer | XL | 0.32 |

Lenalidomide in crystal form α was used, and a weight-average molecular weight of the hydroxypropyl methylcellulose K1500 was about 300,000. A preparation method of tablets was as follows: weighing the above raw materials and excipients excluding the sodium stearyl fumarate, sieving the same with a 60-mesh sieve respectively and mixing uniformly, then adding the sodium stearyl fumarate and mixing properly, and pressing the mixture into tablets with a hardness of 4 kg/cm² to 5 kg/cm² and a density of 0.871 g/cm³.

Floating performance of gastro-floating sustained-release tablet in Embodiment 8: the tablet floated up quickly after being put into a dissolution cup, and floated continuously in a dissolution medium for at least 24 hours.

Determination Results of Release Rate of the Lenalidomide Gastro-Retentive Sustained-Release Tablets Prepared According to Embodiment 8:

| Time (h) | 2 | 4 | 8 | 12 | 16 | 20 | 24 |
|---|---|---|---|---|---|---|---|
| Drug release percentage (%) | 19.5 | 33.9 | 59.4 | 76.1 | 88.2 | 94.9 | 94.7 |

The determination results show that the lenalidomide gastro-retentive sustained-release tablet has a significant sustained-release characteristic, and it will take about 14 hours to release 80% of the drugs in the tablet.

Embodiment 9

| Lenalidomide | 30 g |
|---|---|
| Sodium carboxymethylcellulose | 82 g |
| Microcrystalline cellulose | 79 g |
| Hydroxypropyl cellulose | 92 g |
| Silicon dioxide | 7 g |
| Magnesium stearate | 7 g |
| Finished products | 1000 tablets |

Information of Release Enhancer and Sustained-Release Material:

| Trade name | Category | Model | Bulk density (g/cm³) |
|---|---|---|---|
| Sodium carboxymethylcellulose | Sustained-release material | SJJ-H | 0.51 |
| Microcrystalline cellulose | Release enhancer | 101 | 0.39 |
| Hydroxypropyl cellulose | Sustained-release material | HF | 0.42 |

Lenalidomide in crystal form B was used. A preparation method of tablets was as follows: weighing the above raw materials and excipients excluding the magnesium stearate, sieving the same with a 60-mesh sieve respectively and mixing uniformly, then adding the magnesium stearate and mixing properly, and pressing the mixture into tablets with a hardness of 5 kg/cm² to 6 kg/cm² and a density of 0.967 g/cm³. Floating performance of gastro-floating sustained-release tablet in Embodiment 9: the tablet floated up quickly after being put into a dissolution cup, and floated continuously in a dissolution medium for at least 24 hours.

Determination Results of Release Rate of the Lenalidomide Gastro-Retentive Sustained-Release Tablets Prepared According to Embodiment 9:

| Time (h) | 2 | 4 | 8 | 12 | 16 | 20 | 24 |
|---|---|---|---|---|---|---|---|
| Drug release percentage (%) | 18.9 | 28.9 | 47.2 | 65 | 77.9 | 88.6 | 94.2 |

The determination results show that the lenalidomide gastro-retentive sustained-release tablet has a significant sustained-release characteristic, and it will take about 18 hours to release 80% of the drugs in the tablet.

Embodiment 10

| Lenalidomide | 25 g |
|---|---|
| Microcrystalline cellulose | 26 g |
| Hydroxypropyl methylcellulose | 68 g |
| Hydroxyethyl cellulose | 46 g |
| Silicon dioxide | 2 g |
| Magnesium stearate | 2 g |
| Finished products | 1000 tablets |

Information of Release Enhancer and Sustained-Release Material:

| Trade name | Category | Model | Bulk density (g/cm³) |
|---|---|---|---|
| Hydroxypropyl methylcellulose | Sustained-release material | K750 | 0.29 |
| Microcrystalline cellulose | Release enhancer | 101 | 0.39 |
| Hydroxyethyl cellulose | Sustained-release material | HHW | 0.51 |

Lenalidomide in crystal form F was used. A preparation method of tablets was as follows: weighing the above raw materials and excipients excluding the magnesium stearate, sieving the same with a 60-mesh sieve respectively and mixing uniformly, then adding the magnesium stearate and mixing properly, and pressing the mixture into tablets with a hardness of 5 kg/cm² to 6 kg/cm² and a density of 0.975 g/cm³. Floating performance of gastro-floating sustained-release tablet in Embodiment 10: the tablet floated up quickly after being put into a dissolution cup, and floated continuously in a dissolution medium for at least 24 hours.

Determination Results of Release Rate of the Lenalidomide Gastro-Retentive Sustained-Release Tablets Prepared According to Embodiment 10:

| Time (h) | 2 | 4 | 8 | 12 | 16 | 20 | 24 |
|---|---|---|---|---|---|---|---|
| Drug release percentage (%) | 29.8 | 43.5 | 68 | 85.4 | 94.7 | 95.2 | 95.8 |

The determination results show that the lenalidomide gastro-retentive sustained-release tablet has a significant sustained-release characteristic, and it will take about 10 hours to release 80% of the drugs in the tablet.

Embodiment 11

| Lenalidomide | 25 g |
|---|---|
| Sodium carboxymethylcellulose | 82 g |
| Microcrystalline cellulose | 18 g |
| Hydroxypropyl methylcellulose | 85 g |
| Crospovidone | 152 g |
| Silicon dioxide | 7 g |
| Magnesium stearate | 7 g |
| Finished products | 1000 tablets |

Information of Release Enhancer and Sustained-Release Material:

| Trade name | Category | Model | Bulk density (g/cm³) |
|---|---|---|---|
| Sodium carboxymethylcellulose | Sustained-release material | SJJ-H | 0.51 |
| Microcrystalline cellulose | Release enhancer | 101 | 0.39 |
| Hydroxypropyl methylcellulose | Sustained-release material | K200M | 0.29 |
| Crospovidone | Release enhancer | XL | 0.32 |

Lenalidomide in crystal form B was used, and a weight-average molecular weight of the hydroxypropyl methylcellulose K200M was about 1,200,000. A preparation method of tablets was as follows: weighing the above raw materials and excipients excluding the magnesium stearate, sieving the same with a 60-mesh sieve respectively and mixing uniformly, then adding the magnesium stearate and mixing properly, and pressing the mixture into tablets with a hardness of 7 kg/cm² to 8 kg/cm² and a density of 0.968 g/cm³.

Floating performance of gastro-floating sustained-release tablet in Embodiment 11: the tablet floated up quickly after being put into a dissolution cup, and floated continuously in a dissolution medium for at least 24 hours.

Determination Results of Release Rate of the Lenalidomide Gastro-Retentive Sustained-Release Tablets Prepared According to Embodiment 11:

| Time (h) | 2 | 4 | 8 | 12 | 16 | 20 | 24 |
|---|---|---|---|---|---|---|---|
| Drug release percentage (%) | 25.7 | 40.1 | 62.9 | 79.0 | 88.8 | 94.9 | 97.2 |

The determination results show that the lenalidomide gastro-retentive sustained-release tablet has a significant sustained-release characteristic, and it will take about 12 hours to release 80% of the drugs in the tablet.

In order to further illustrate that the lenalidomide gastro-retentive sustained-release tablet of the present invention has the beneficial effect of gastro-retention, ordinary lenalidomide sustained-release tablets were prepared as a comparative example. Please refer to Embodiment 5 for a prescription of the ordinary sustained-release tablets (Embodiment 12), and the difference is that the microcrystalline cellulose in Embodiment 5 is replaced by lactose with high bulk density (the lactose and the microcrystalline cellulose are used in an original capsule preparation). Please refers to Embodiment 8 for a prescription of the ordinary sustained-release tablets (Embodiment 13), and the difference is that the sustained-release material in Embodiment 13 is replaced by the hydroxyethyl cellulose with high bulk density.

Embodiment 12 Ordinary Lenalidomide Sustained-Release Tablet

| Lenalidomide | 25 g |
|---|---|
| Lactose | 220 g |
| Hydroxypropyl methylcellulose (K100M) | 75 g |
| Silicon dioxide | 2 g |
| Magnesium stearate | 2 g |
| Finished products | 1000 tablets |

Lenalidomide in crystal form B was used. A preparation method of tablets was as follows: weighing the above raw materials and excipients excluding the magnesium stearate, sieving the same with a 60-mesh sieve respectively and mixing uniformly, then adding the magnesium stearate and mixing properly, and pressing the mixture into tablets with a hardness of 7 kg/cm² to 8 kg/cm² and a density of 1.158 g/cm³. Floating performance of the ordinary sustained-release tablet: the tablet sunk after being put into a dissolution cup, and didn't float within 24 hours.

Determination Results of Release Rate of the Ordinary Lenalidomide Sustained-Release Tablet:

| Time (h) | 2 | 4 | 8 | 12 | 16 | 20 | 24 |
|---|---|---|---|---|---|---|---|
| Drug release percentage (%) | 15 | 25.9 | 43.4 | 58.1 | 73.8 | 84.7 | 93.6 |

The determination results show that the ordinary lenalidomide sustained-release tablet has a significant sustained-release characteristic, and it will take about 18 hours to release 80% of the drugs in the tablet. However, the ordinary sustained-release tablet has no floating performance and cannot implement a gastro-retentive effect.

Embodiment 13 Ordinary Lenalidomide Sustained-Release Tablet

| | |
|---|---|
| Lenalidomide | 25 g |
| Crospovidone | 74 g |
| Hydroxyethyl cellulose | 98 g |
| Silicon dioxide | 2 g |
| Sodium stearyl fumarate | 2 g |
| Finished products | 1000 tablets |

Information of Release Enhancer and Sustained-Release Material:

| Trade name | Category | Model | Bulk density (g/cm$^3$) |
|---|---|---|---|
| Hydroxyethyl cellulose | Sustained-release material | HX | 0.55 |
| Crospovidone | Release enhancer | XL | 0.32 |

Lenalidomide in crystal form α was used. A preparation method of tablets was as follows: weighing the above raw materials and excipients excluding the sodium stearyl fumarate, sieving the same with a 60-mesh sieve respectively and mixing uniformly, then adding the sodium stearyl fumarate and mixing properly, and pressing the mixture into tablets with a hardness of 4 kg/cm$^2$ to 5 kg/cm$^2$ and a density of 1.098 g/cm$^3$.

Floating performance of gastro-floating sustained-release tablet in Embodiment 13: the tablet didn't float within 24 hours after being put into a dissolution cup.

Determination Results of Release Rate of the Lenalidomide Gastro-Retentive Sustained-Release Tablet Prepared According to Embodiment 13:

| Time (h) | 2 | 4 | 8 | 12 | 16 | 20 | 24 |
|---|---|---|---|---|---|---|---|
| Drug release percentage (%) | 14.6 | 24.2 | 42.4 | 59.0 | 72.6 | 84.3 | 92.7 |

The determination results show that the lenalidomide gastro-retentive sustained-release tablet has a significant sustained-release characteristic, and it will take about 20 hours to release 80% of the drugs in the tablet.

Comparative Test of Pharmacokinetic Parameters of Lenalidomide Preparation

Test Samples:
(1) Quick-release capsule: lenalidomide capsule (Revlimid, specification: 25 mg) produced by Celgene Biopharmaceutical Company in America;
(2) Ordinary sustained-release tablet: Embodiment 12 (specification: 25 mg); and
(3) Gastro-retentive sustained-release tablet: Embodiment 5 (specification: 25 mg).

Test Method:
Eighteen Beagle dogs were randomly divided into three groups, and one unit preparation of a commercially available lenalidomide quick-release capsule, the ordinary lenalidomide sustained-release tablet and the lenalidomide gastro-retentive sustained-release tablet of the present invention were administrated respectively to the dogs in each group. Concentrations of the lenalidomide in plasma at different time points after administration were determined by high performance liquid chromatography, and pharmacokinetic parameters were calculated. See the following table for details:

| Pharmacokinetic parameter | Quick-release capsule | Ordinary sustained-release tablet | Gastro-retentive sustained-release tablet |
|---|---|---|---|
| Tmax (hr) | 1.5 | 2.6 | 4.6 |
| Cmax (ng/mL) | 388 ± 95 | 145 ± 35 | 155 ± 32 |
| $t_{1/2}$ (hr) | 2.7 | 4.9 | 8.8 |
| AUC (ng · hr/mL) | 1527 ± 201 | 1106 ± 131 | 1506 ± 125 |

The results show that a time peak (Tmax) of the lenalidomide is effectively delayed and a peak concentration (Cmax) is significantly reduced by the lenalidomide gastro-retentive sustained-release tablet in comparison to the lenalidomide quick-release capsule. A bioavailability (AUC) of the gastro-retentive sustained-release tablet is significantly higher than that of the ordinary sustained-release tablet.

In order to further illustrate that the lenalidomide gastro-retentive sustained-release tablet of the present invention has a better stability than the ordinary gastro-floating tablet added with a floating assistant or a foaming agent, the ordinary gastro-floating tablet added with the foaming agent and the floating assistant (waxy material) was prepared, and an accelerated stability comparison study was performed on the ordinary lenalidomide gastro-floating tablet and the gastro-retentive sustained-release tablet of the present invention.

Embodiment 14 Ordinary Lenalidomide Gastro-Floating Tablet Added with Floating Assistant (Octadecanol)

| | |
|---|---|
| Lenalidomide | 25 g |
| Octadecanol | 90 g |
| Microcrystalline cellulose | 140 g |
| Hydroxypropyl methylcellulose (K100M) | 75 g |
| Silicon dioxide | 2 g |
| Magnesium stearate | 2 g |
| Finished products | 1000 tablets |

Lenalidomide in crystal form B was used. A preparation method of tablets was as follows: weighing the above raw materials and excipients excluding the magnesium stearate, sieving the same with a 60-mesh sieve respectively and mixing uniformly, then adding the magnesium stearate and mixing properly, and pressing the mixture into tablets with a hardness of 7 kg/cm$^2$ to 8 kg/cm$^2$ and a density of 0.928 g/cm$^3$. Embodiment 15 Ordinary lenalidomide gastro-floating tablet added with foaming

| agent (calcium carbonate): | |
|---|---|
| Lenalidomide | 25 g |
| Calcium carbonate | 50 g |
| Microcrystalline cellulose | 172 g |
| Hydroxypropyl methylcellulose (K100M) | 75 g |

-continued

| agent (calcium carbonate): | |
|---|---|
| Silicon dioxide | 2 g |
| Magnesium stearate | 2 g |
| Finished products | 1000 tablets |

Lenalidomide in crystal form B was used. A preparation method of tablets was as follows: weighing the above raw materials and excipients excluding the magnesium stearate, sieving the same with a 60-mesh sieve respectively and mixing uniformly, then adding the magnesium stearate and mixing properly, and pressing the mixture into tablets with a hardness of 7 kg/cm² to 8 kg/cm² and a density of 1.098 g/cm³.

Accelerated stability test conditions: a temperature of 40□±2□, and a relative humidity of 75%±5%, wherein zero-month sample inspection was performed before setting out, and sampling inspection was performed in first, second, third and sixth months after setting out.

Inspection Results of Stability Test:
Change Results of Lenalidomide Content in Samples:

| | Inspection time point | | | | |
|---|---|---|---|---|---|
| Tablet type | Zero month | First month | Second month | Third month | Sixth month |
| Gastro-retentive sustained-release tablet of the present invention | 99.9% | 99.8% | 99.6% | 99.5% | 99.0% |
| Ordinary gastro-floating tablet added with floating assistant | 99.7% | 99.2% | 98.6% | 97.7% | 94.0% |
| Ordinary gastro-floating tablet added with foaming agent | 99.2% | 95.2% | 90.6% | 87.7% | 80.1% |

Change Results of Total Related Substances in Samples:

| | Inspection time point | | | | |
|---|---|---|---|---|---|
| Tablet type | Zero month | First month | Second month | Third month | Sixth month |
| Gastro-retentive sustained-release tablet of the present invention | 0.15% | 0.19% | 0.24% | 0.26% | 0.31% |
| Ordinary gastro-floating tablet added with floating assistant | 0.14% | 0.28% | 0.37% | 0.51% | 1.06% |
| Ordinary gastro-floating tablet added with foaming agent | 0.25% | 1.89% | 3.57% | 5.81% | 15.4% |

The stability inspection results show that the content of the ordinary gastro-floating tablet added with the foaming agent is decreased significantly during the accelerated test, while the contents of the related substances are increased significantly. The content of the ordinary gastro-floating tablet added with the floating assistant is also decreased significantly, while the contents of the related substances are increased significantly. However, the content of the gastro-retentive sustained-release tablet of the present invention is stable and does not change obviously, while the contents of the related substances are slightly increased. The stability of the lenalidomide gastro-retentive sustained-release tablet of the present invention is obviously superior to that of the ordinary gastro-floating tablet added with the floating assistant or the ordinary gastro-floating tablet added with the foaming agent.

The invention claimed is:

1. A lenalidomide gastro-retentive sustained-release tablet, wherein the sustained-release tablet consists of 3 wt % to 14 wt % of crystalline lenalidomide, 14 wt % to 68 wt % of release enhancer with low bulk density, 23 wt % to 70 wt % of sustained-release material with low bulk density, and the balance of other pharmaceutically acceptable excipients, wherein the bulk density of the release enhancer ranges from 0.24 g/cm³ to 0.52 g/cm³; and the bulk density of the sustained release material ranges from 0.29 g/cm³ to 0.51 g/cm³,
    wherein the release enhancer is one or more selected from the group consisting of crospovidone, microcrystalline cellulose and croscarmellose sodium,
    wherein the sustained-release material is one or more selected from the group consisting of hydroxypropyl methylcellulose, polyethylene oxide, hydroxypropyl cellulose, hydroxyethyl cellulose and sodium carboxymethylcellulose,
    wherein the other pharmaceutically acceptable excipients comprise a lubricant and a glidant, the lubricant including one or more selected from the group consisting of magnesium stearate, sodium stearyl fumarate and talcum, and the glidant including one or more selected from the group consisting of silicon dioxide and talcum,
    wherein the hardness of the lenalidomide gastro-retentive sustained-release tablet ranges from 3 kg/cm² to 10 kg/cm²,
    wherein a density of the lenalidomide gastro-retentive sustained-release tablet ranges from 0.755 g/cm³ to 0.991 g/cm³, and
    wherein the lenalidomide gastro-retentive sustained-release tablet does not contain floating assistants and alkaline foaming agents, the floating assistants being octadecanol, stearic acid, glyceryl monostearate, glyceryl behenate, carnauba wax, white wax and hydrogenated vegetable oil, the alkaline foaming agents being alkaline carbonate and bicarbonate.

2. The lenalidomide gastro-retentive sustained-release tablet according to claim 1, wherein the sustained-release material is hydroxypropyl methylcellulose, and a weight-average molecular weight thereof is greater than or equal to 200,000.

3. The lenalidomide gastro-retentive sustained-release tablet according to claim 1, wherein a viscosity of 2% aqueous solution of the sodium carboxymethylcellulose, the hydroxypropyl cellulose and the hydroxyethyl cellulose is greater than 3000 mPa·s.

4. A coated lenalidomide gastro-retentive sustained-release tablet comprising:
    the lenalidomide gastro-retentive sustained-release tablet according to claim 1; and
    a coating layer coating the lenalidomide gastro-retentive sustained-release tablet,
    wherein the coating layer comprises lenalidomide.

5. A lenalidomide gastro-retentive sustained-release tablet, wherein the sustained-release tablet comprises 3 wt % to 14 wt % of crystalline lenalidomide, 14 wt % to 68 wt % of release enhancer with low bulk density, 23 wt % to 70 wt % of sustained-release material with low bulk density, and the balance of other pharmaceutically acceptable excipients, wherein lenalidomide in the lenalidomide gastro-retentive sustained-release tablet consists of the crystalline lenalidomide, wherein the bulk density of the release enhancer ranges from 0.24 g/cm$^3$ to 0.52 g/cm$^3$; and the bulk density of the sustained release material ranges from 0.29 g/cm$^3$ to 0.51 g/cm$^3$, wherein the release enhancer is one or more selected from the group consisting of crospovidone, microcrystalline cellulose and croscarmellose sodium, wherein the sustained-release material is one or more selected from the group consisting of hydroxypropyl methylcellulose, polyethylene oxide, hydroxypropyl cellulose, hydroxyethyl cellulose and sodium carboxymethylcellulose, wherein the other pharmaceutically acceptable excipients comprise a lubricant and a glidant, the lubricant including one or more selected from the group consisting of magnesium stearate, sodium stearyl fumarate and talcum, and the glidant including one or more selected from the group consisting of silicon dioxide and talcum, wherein the hardness of the lenalidomide gastro-retentive sustained-release tablet ranges from 3 kg/cm$^2$ to 10 kg/cm$^2$, wherein a density of the lenalidomide gastro-retentive sustained-release tablet ranges from 0.755 g/cm$^3$ to 0.991 g/cm$^3$, and wherein the lenalidomide gastro-retentive sustained-release tablet does not contain floating assistants and alkaline foaming agents, the floating assistants being octadecanol, stearic acid, glyceryl monostearate, glyceryl behenate, carnauba wax, white wax and hydrogenated vegetable oil, the alkaline foaming agents being alkaline carbonate and bicarbonate.

6. The lenalidomide gastro-retentive sustained-release tablet according to claim 5, wherein the sustained-release material is hydroxypropyl methylcellulose, and a weight-average molecular weight thereof is greater than or equal to 200,000.

7. The lenalidomide gastro-retentive sustained-release tablet according to claim 5, wherein a viscosity of 2% aqueous solution of the sodium carboxymethylcellulose, the hydroxypropyl cellulose and the hydroxyethyl cellulose is greater than 3000 mPa·s.

8. A lenalidomide gastro-retentive sustained-release tablet, wherein the sustained-release tablet comprises 3 wt % to 14 wt % of lenalidomide, 14 wt % to 68 wt % of release enhancer with low bulk density, 23 wt % to 70 wt % of sustained-release material with low bulk density, and the balance of other pharmaceutically acceptable excipients, wherein the bulk density of the release enhancer ranges from 0.24 g/cm$^3$ to 0.52 g/cm$^3$; and the bulk density of the sustained release material ranges from 0.29 g/cm$^3$ to 0.51 g/cm$^3$, wherein the release enhancer is one or more selected from the group consisting of crospovidone, microcrystalline cellulose and croscarmellose sodium, wherein the sustained-release material includes one or more selected from the group consisting of polyethylene oxide, hydroxypropyl cellulose, hydroxyethyl cellulose and sodium carboxymethylcellulose, wherein the other pharmaceutically acceptable excipients comprise a lubricant and a glidant, the lubricant including one or more selected from the group consisting of magnesium stearate, sodium stearyl fumarate and talcum, and the glidant including one or more selected from the group consisting of silicon dioxide and talcum, wherein the hardness of the lenalidomide gastro-retentive sustained-release tablet ranges from 3 kg/cm$^2$ to 10 kg/cm$^2$, wherein a density of the lenalidomide gastro-retentive sustained-release tablet ranges from 0.755 g/cm$^3$ to 0.991 g/cm$^3$, and wherein the lenalidomide gastro-retentive sustained-release tablet does not contain floating assistants and alkaline foaming agents, the floating assistants being octadecanol, stearic acid, glyceryl monostearate, glyceryl behenate, carnauba wax, white wax and hydrogenated vegetable oil, the alkaline foaming agents being alkaline carbonate and bicarbonate.

9. The lenalidomide gastro-retentive sustained-release tablet according to claim 8, wherein a viscosity of 2% aqueous solution of the sodium carboxymethylcellulose, the hydroxypropyl cellulose and the hydroxyethyl cellulose is greater than 3000 mPa·s.

10. The lenalidomide gastro-retentive sustained-release tablet according to claim 1, wherein the other pharmaceutically acceptable excipients consists of the lubricant and the glidant.

* * * * *